United States Patent [19]

Ratcliffe et al.

[11] Patent Number: 4,570,020

[45] Date of Patent: Feb. 11, 1986

[54] PRODUCTION OF METHANETHIOL FROM $H_2S$ AND CO

[75] Inventors: Charles T. Ratcliffe, Pittstown, N.J.; Petrus J. Tromp, Amsterdam, Netherlands; Israel E. Wachs, Bridgewater, N.J.

[73] Assignee: Exxon Research and Engineering Co., Florham Park, N.J.

[21] Appl. No.: 626,065

[22] Filed: Jun. 29, 1984

[51] Int. Cl.$^4$ .................. C07C 149/06; C07C 149/10
[52] U.S. Cl. ................................ 568/70; 423/648 R; 568/60; 585/733
[58] Field of Search ............... 568/60, 70; 423/648 R; 585/733

[56] References Cited

U.S. PATENT DOCUMENTS

| | | | |
|---|---|---|---|
| 3,856,925 | 12/1974 | Kodera et al. | 423/416 |
| 3,963,785 | 6/1976 | Kubicek | 260/609 B |
| 4,151,191 | 4/1979 | Happel et al. | 48/197 |
| 4,235,699 | 11/1980 | Ratcliffe et al. | 208/56 |
| 4,238,370 | 12/1980 | Konig | 252/461 |
| 4,326,081 | 4/1982 | Ratcliffe et al. | 564/417 |

OTHER PUBLICATIONS

Fukuda et al., "Catalytic Activity of Metal Sulfides for the Reaction $H_2S+CO=H_2+COS$", *J. Catalysis* V49, 378-82 (1977).

Dokiya, et al., "The Study of Thermochemical Hydrogen Preparation, VI, A Hydrogen-Evolving Step Through the $H_2S$-CO Cycle", *J. Bull. Chem. Soc. Japan,* V51 (1), 150-3 (1978).

M. Inomata et al., J. Phys. Chem. (1983), 87(5), 754-61, Structures of Supported Vanadium Oxide Catalysts, 1, Vanadium (v) Oxide/Titanium Dioxide (Anatase) Vanadium (v) Oxide/Titanium Dioxide (Rutile), and Vanadium (v) Oxide/Titanium Dioxide (Mixture of Anatase with Rutile.

*Primary Examiner*—Donald G. Daus
*Assistant Examiner*—Mary E. Ceperley
*Attorney, Agent, or Firm*—Edward M. Corcoran

[57] ABSTRACT

Methanethiol is produced from a gaseous feed comprising a mixture of $H_2S$ and CO by contacting said feed, at a temperature of at least about 225° C., with a catalyst comprising an oxide of a metal selected from the group consisting of V, Nb, and Ta and mixtures thereof, preferably V, supported on titania and wherein at least a portion, and preferably at least about 25 wt. %, of said supported oxide is in a non-crystalline form.

23 Claims, 1 Drawing Figure

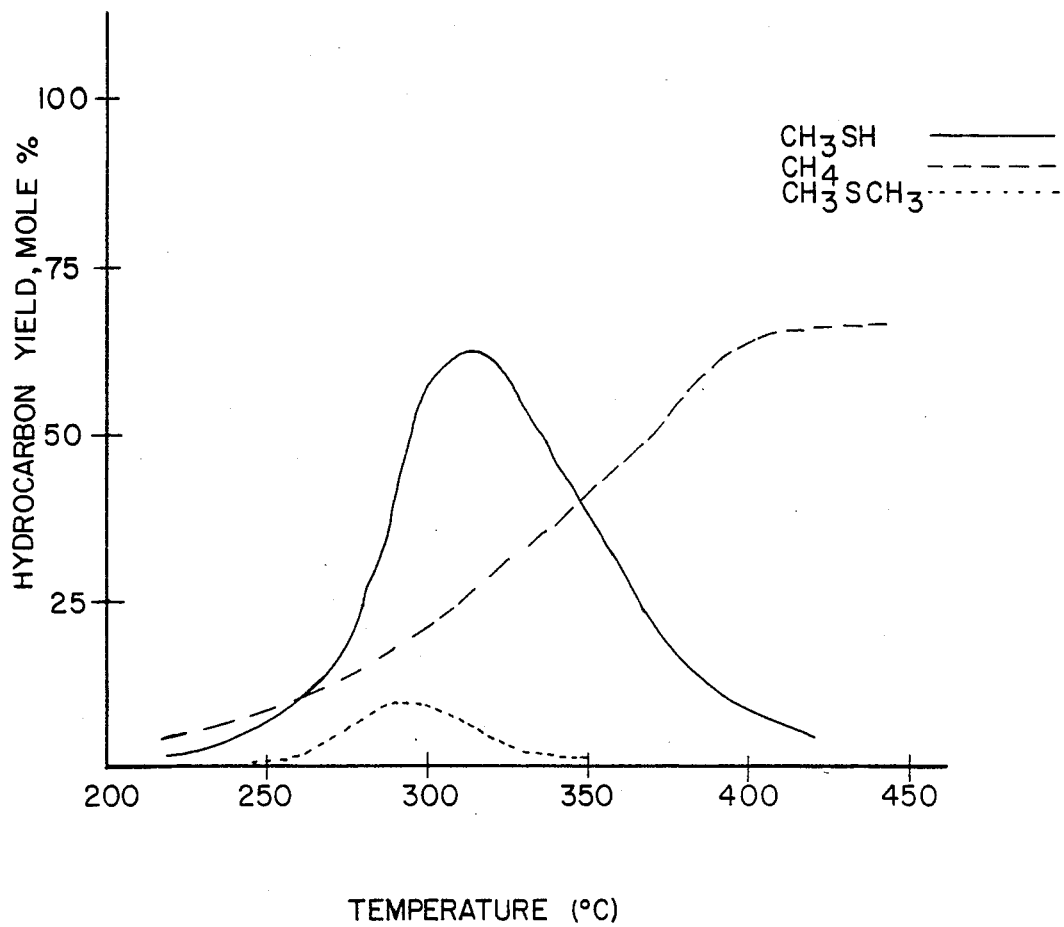
HYDROCARBON PRODUCT DISTRIBUTION H₂S/CO REDUCTION OVER 2% V₂O₅ ON TiO₂

PRODUCTION OF METHANETHIOL FROM H₂S AND CO

BACKGROUND OF THE INVENTION

1. Field of the Invention

This invention relates to producing methanethiol from $H_2S$ and CO. More particularly, this invention relates to producing methanethiol by passing a gas feed comprising a mixture of $H_2S$ and CO over a catalyst comprising an oxide of a metal selected from the group consisting of V, Nb, Ta and mixture thereof supported on titania, at a temperature of at least about 225° C., for a time sufficient to convert at least a portion of said feed to methanethiol.

2. Background of the Disclosure

Hydrogen sulfide is an unwanted by-product of many refinery processes, being very toxic and having few practical uses. In many cases, $H_2S$ is disposed of by the Claus Process in which a portion of the $H_2S$ is oxidized to $SO_2$. The remaining $H_2S$ is then reacted with the $SO_2$ in the presence of a suitable catalyst to produce $H_2O$ and elemental sulfur. $H_2S$ can also be reacted with oxygen in the presence of an iron oxide catalyst to form water and elemental sulfur.

Some uses of $H_2S$ include conversion of mononitro aromatic compounds to amino compounds as disclosed in U.S. Pat. No. 4,326,081. In U.S. Pat. No. 4,235,699, Ratcliffe, et al. disclose forming lower molecular weight products from coal and coal tar using a mixture of CO and $H_2S$ as a hydrogenating agent. Fukuda, et al. in "Catalytic Activity of Metal Sulfides for the Reaction, $H_2S+CO=H_2+COS$", J. Catalysis 49, p. 379–382 (1977), studied first row transition metal sulfides as catalysts for producing COS and $H_2$ from mixtures of $H_2S$ and CO (see also Masayuki, et al., "The Study of Thermochemical Hydrogen Preparation. VI. A Hydrogen-evolving Step Through the $H_2S$-CO Cycle", Bull. Chem. Soc. Japan, 51 (1) p. 150–153 [1978]).

More recently, Happel, et al. in U.S. Pat. No. 4,151,191 have disclosed the use of sulfur resistant catalysts for methane production in the presence of $H_2S$. This reference discloses producing methane from a feed mixture containing $H_2$, CO and gaseous sulfur compounds, such as $H_2S$, by contacting the feed with a predominantly molybdenum oxide catalyst containing at least one element of lanthanide or actenide groups of elements at a temperature of about at least 300° C. U.S. Pat. No. 3,963,785 discloses the synthesis of aliphatic thiols by reacting $H_2S$ with olefins or aldehydes in the presence of $CS_2$. Finally, Kodera, et al. in U.S. Pat. No. 3,856,925 disclose the manufacture of $H_2$ and COS from mixtures of $H_2S$ and CO using various Group VB, VIB and VIII metal sulfides as catalysts.

SUMMARY OF THE INVENTION

The present invention relates to producing methanethiol, $CH_3SH$, from a gaseous feed comprising a mixture of $H_2S$ and CO by contacting said feed, at a temperature of at least about 225° C., with a catalyst comprising an oxide of a metal selected from the group consisting of V, Nb, Ta and mixture thereof supported on titania for a time sufficient to convert at least a portion of said CO and $H_2S$ to methanethiol and wherein at least a portion of said oxide, preferably at least about 25 wt.% of said oxide, is in a non-crystalline form. In a preferred embodiment the catalyst will comprise an oxide of vanadium supported on titania. Thus, in a preferred embodiment the catalyst will comprise an oxide of a metal selected from the group consisting of (a) V and (b) mixtures of V with Nb, Ta and mixtures thereof supported on titania wherein at least a portion of said oxide is in a non-crystalline form. Again, it is preferred that at least about 25 wt.% of said supported oxide is in a non-crystalline form. Further, the titania may be mixed with other suitable inorganic refractory oxides which serve merely as a diluent and which do not have any adverse effect on the process of this invention.

BRIEF DESCRIPTION OF THE DRAWING

The FIGURE is a graph illustrating mole % product distribution as a function of reaction temperature of products formed by reacting a mixture of $H_2S$ and CO in the presence of a catalyst comprising 2 wt.% vanadium oxide on titania.

DETAILED DESCRIPTION

Those skilled in the art know that methanethiol or methyl mercaptan is used as an odorant or tracer for natural gas and is also used as a raw material in the manufacture of methionine, fungicides and jet fuel additives.

As stated above, the present invention relates to producing methanethiol from a gaseous feed comprising a mixture of $H_2S$ and CO by contacting said feed with a catalyst comprising an oxide of a metal selected from the group consisting of V, Nb, Ta and mixtures thereof supported on titania at a temperature of at least about 225° C. wherein at least a portion, and preferably at least about 25 wt.%, of said supported oxide is in a non-crystalline form. In a preferred embodiment the catalyst will comprise an oxide of a metal selected from the group consisting of (a) V and (b) mixtures of V with Nb, Ta and mixtures thereof supported on titania wherein at least a portion of said oxide is in a non-crystalline form. Again, it is preferred that at least about 25 wt.% of said supported oxide is in a non-crystalline form. As a practical matter, a minor amount of methyl sulfide, $(CH_3)_2S$, will also be produced by the process of this invention as can be seen from the FIGURE. The amount of methyl sulfide produced by this process depends on the reaction conditions employed and initially increases with increasing reaction temperature and then peaks and at higher temperatures decreases.

Thus, the catalysts useful in the process of this invention comprise titania whose surface has been modified with an oxide of a Group VA metal (vanadium, niobium, tantalum, and mixture thereof). That is, the surface of the titania has been modified by an oxide of vanadium, niobium, tantalum and mixture thereof in an amount such that the catalyst exhibits properties different from titania whose surface has not been modified and different from bulk oxides of vanadium, niobium, tantalum and mixture thereof. Consequently, the Group VA metal oxide loading on the titania must be sufficient to modify the titania surface, but not enough to result in a catalyst exhibiting properties of the bulk oxides of vanadia, niobia, tantala and mixtures thereof. Thus, at least a portion of and preferably at least about 25 wt.% of the Group VA metal oxide will be in a non-crystalline form. This will be accomplished if the metal oxide loading on the titania broadly ranges between about 0.5 to 25 wt.% of the total catalyst weight.

As previously stated, the process of this invention will occur at an elevated temperature of at least about 225° C. Referring to the FIGURE, one can readily see that the onset of methanethiol production starts to occur at a temperature of about 225° C., and more preferably about 250° C., and reaches a peak (under the particular reaction conditions and feed mixture set forth in the FIGURE) or optimum at a temperature of about 325° C. However, as previously stated, methanethiol is thermally unstable at 350° C. Therefore, if the reaction temperature approaches and/or exceeds this temperature, one must take provisions to rapidly quench the so-formed methanethiol down to a temperature below about 350° C. in order to prevent thermal decomposition thereof.

Referring again to the FIGURE, one can see that methane is also produced as a result of reacting a gaseous feed comprising a mixture of CO and $H_2S$ in the presence of a catalyst of this invention. However, one can also see that a different temperature regime applies to the production of methane. To produce predominantly methane and hydrogen, one would preferably conduct the reaction at a temperature above about 300° C. and even more preferably above about 350° C.

The catalysts of this invention may be prepared by techniques well-known in the art, such as incipient wetness, impregnation, etc., the choice being left to the practitioner. When using the impregnation technique, the impregnating solution is contacted with the titania support material for a time sufficient to deposit the precursor material onto the support either by selective adsorption or alternatively, the excess solvent may be evaporated during drying leaving behind the precursor salt. If an impregnation or incipient wetness technique is used to prepare a catalyst of this invention, the transition metal oxide precursor salt solution used may be aqueous or organic, the only requirement being that an adequate amount of precursor compound for the selected transition metal oxide be soluble in the solvent used in preparing this solution.

The final catalyst composite will then normally be dried at temperatures ranging from about 50°–300° C. to remove the excess solvent and, if necessary, decompose the salt if it is an organic salt to form a catalyst precursor. The precursor is then converted into the catalyst by calcining at temperatures of from about 150° to 800° C. and preferably 300°–700° C. in a suitable oxidizing atmosphere such as air, oxygen, etc. The time required to calcine the composite will, of course, depend on the temperature and in general will range from about 0.5–7 hours. Reducing atmospheres may also be used to decompose the transition metal oxide precursors, but the resulting composite will then require subsequent calcination to convert the reduced metal component to the oxide form.

The catalysts of this invention will generally have metal oxide loadings of from about 0.5 to 25 wt.% metal oxide based on the total catalyst composition, preferably from about 1 to 15 wt.%, more preferably from about 2–10 wt.% based on the total catalyst composition.

In general, the ratio of $H_2S$ to CO in the gaseous feed used in the process of this invention will typically range from about 1/4 to 40/1 and more preferably from about 1/2 to 4/1 on a mole basis. It has been found experimentally that a 1/1 ratio appears to be the optimum for maximum conversion of the feed. The reaction temperature will generally range from about 225° to 450° C., preferably 250° to 400° C. and still more preferably from about 300° to 400° C. However, as previously stated, exceeding a reaction temperature of 350° C. may necessitate a quenching of the $CH_3SH$ product in order to avoid its thermal decomposition. With regard to the space velocity of the feed, it is understood that longer contact times will result in a greater amount of product. However, this may be offset by decomposition of $CH_3SH$ product in contact with the catalyst. In general, the space velocity will be maintained below about 4800 V/V/hr.

Because the process of this reaction is a gas phase reaction, the partial pressure of the $H_2S$ is limited to a maximum of approximately 260 psig, which is the pressure at which $H_2S$ liquifies. Accordingly, one will not want to exceed a partial pressure of 260 psig for the $H_2S$ in the feed gas unless it is desired that the reaction occur in the presence of both gaseous and liquid phases.

The invention will be more readily understood by reference to the examples.

EXAMPLES

Experimental

Hydrogen sulfide was obtained in compressed cylinders from Scientific Gas Products (electronic grade 99.999% purity), while carbon monoxide was purchased from Matheson Gas (99.99% purity). The above gases were checked for absence of hydrocarbon impurities (MS analysis and G.C. analysis with FID detector) and used without further purification. Helium (99.99%), when used as an inert carrier gas, was predried in a molecular sieve trap, scrubbed for $O_2$ removal in a hot Cu trap, and redried in a molecular sieve trap. Gas flows were regulated with Tylan F-260 flow controllers and premixed in a gas manifold system prior to entering into the catalyst bed.

A quartz reactor tube of 9 mm ID by 700 mm was loaded with 2.5 gram samples of $-40/+60$ mesh (Tyler) catalyst particles which were supported on each end with degreased quartz wool plugs. An external thermocouple was attached to the outside of the quartz tube near the center of the catalyst bed to record reaction temperature. The tube was heated with a three zone electric furnace (ATS-3210) equipped with Omega set point controllers.

Product analysis was accomplished with an on-line Carle GC (series SX) equipped with a hydrogen transfer system and FID/TC detectors. Gas phase samples were also separated on a Perkin Elmer 900 GC coupled to a DuPont 21-491 mass spectrometer for product identification of $CH_3SH$ and $CH_3SCH_3$. Response factors for quantitative G.C. analysis were obtained from a primary standard mixture of gases with quantities similar to the product mixture.

Catalyst Preparation

Degussa P-25, a mixture of anatase and rutile titania, was used as the titania support. All of the catalysts were prepared in a glove box in a nitrogen atmosphere to prevent decomposition of the transition metal oxide precursors. In all cases 10 grams of the P-25 titania powder were slurried in 100 cc of ethanol to which was added the transition metal oxide precursor, with the resulting mixture stirred overnight, under flowing nitrogen, to evaporate the ethanol. Each dry mixture was then taken out of the glove box and 3 cc of water added. The resulting mixture was stirred overnight in air, then the dry powder placed in a quartz boat and slowly heated in a 1/1 flowing mixture of $O_2$ in He up to 400° C. At 400° C. the He flow was cut off and the powdered catalyst precursor then heated from 400° to 575° C. in 100% $O_2$. Each sample of catalyst precursor was held at 575° C. in the $O_2$ for two hours to calcine the precursor into a catalyst of this invention.

The transition metal oxide precursors were obtained from Alfa, Inc. and were $Nb(C_2H_5O)_5$, $Ta(C_2H_5O)_5$ and $VO(C_2H_5O)_3$. The amounts of niobia, tantala and vanadia precursors added to each slurry of 10 g P-25 in 100 cc of ethanol were 2.5, 1.84 and 0.46 grams, respectively. The resulting catalysts contained 10 wt.% niobia on titania, 10 wt.% tantala on titania and 2 wt.% vanadia on titania. The niobia, tantala and vanadia contents of the catalysts are expressed as niobium pentoxide, tantalum pentoxide and vanadium pentoxide.

EXAMPLE 1

In this experiment a 2 gram sample of each catalyst was charged to the reactor which was then heated up to a temperature of 200° C. in flowing helium. After the reactor achieved a temperature of 200° C., a 1/1 molar mixture of $H_2S$/CO feed at a flow rate of about 4 cc/min. was introduced to the reactor. The reactor was then held at isothermal conditions in order to establish steady-state conditions with respect to feed conversion and product selectivity. The temperature was then raised at 50° C. intervals and held at each temperature for one hour to measure activity and selectivity. The final temperature reached was 400° C. The reactor was then cooled to 300° C. to recheck the activity compared to the activity during the heating step.

The results are shown in the Table and clearly demonstrate that the catalysts were effective for the conversion of the $H_2S$/CO feed. The vanadia on titania catalyst exhibited much more activity at lower temperatures. This thus indicates that exposure to the feed has an effect of treating or sulfiding the catalyst in-situ to obtain a more active species whose identity is not known. Thus, the catalyst may be pretreated or may be treated in-situ in the reaction zone.

EXAMPLE 2

This experiment was similar to that of Example 1 except that only the vanadia on titania catalyst was used. Also, the amount of $CH_3SCH_3$ in the product, if any, was also measured. The results are shown in the FIGURE.

| $H_2S$ AND CO CONVERSION AS A FUNCTION OF TEMPERATURE[a] | | | |
|---|---|---|---|
| Catalyst | 2% $V_2O_5$/$TiO_2$ | 10% $Nb_2O_5$/$TiO_2$ | 10% $Ta_2O_5$/$TiO_2$ |
| Surface Area[b] | 45 m$^2$/g | 52 m$^2$/g | 54 m$^2$/g |
| Catalyst Weight | 2.0 g | 2.0 g | 2.0 g |
| CO Conversion (%) | | | |
| 300° C. | 36% | — | 9% |
| 300° C. | 35% | 28% | 19% |
| 350° C. | 47% | 40% | 33% |
| 400° C. | 46% | 40% | 33% |
| $H_2S$ Conversion (%) | | | |
| 300° C. | 19% | — | 2.5 |
| 300° C. | 19% | 10 | 8 |
| 350° C. | 23% | 20 | 16 |
| 400° C. | 22% | 20 | 18 |

Notes:
[a]Products included $CH_3SH$ and $CH_4$
[b]BET
[c]After cooling from 400° C.

What is claimed is:

1. A process for producing methanethiol from a gaseous feed comprising a mixture of CO and $H_2S$, said process comprising contacting said feed, at a temperature of at least about 225° C., with a catalyst comprising an oxide of a metal selected from the group consisting of V, Nb, Ta and mixture thereof supported on a support comprising titania for a time sufficient to convert at least a portion of said feed to methanethiol wherein at least a portion of said supported oxide is in a non-crystalline form.

2. The process of claim 1 wherein said reaction temperature ranges between from about 225°–450° C.

3. The process of claim 2 wherein the ratio of $H_2S$ to CO in said gaseous feed ranges between about 1/4 to 40/1 on a mole basis.

4. The process of claim 3 wherein said reaction temperature ranges between about 250°–400° C.

5. The process of claim 4 wherein said ratio of $H_2S$ to CO in said gaseous feed ranges between about 1/2 to 4/1.

6. The process of claim 5 wherein said reaction temperature ranges between about 300° to 400° C.

7. The process of claim 6 wherein at least about 25 wt.% of said supported oxide is in a non-crystalline form.

8. The process of claim 7 wherein said catalyst comprises vanadia on titania.

9. A process for producing methanethiol from a gaseous feed comprising a mixture of CO and $H_2S$, said process comprising contacting said feed at a temperature of at least about 225° C. with a catalyst comprising an oxide of a metal selected from the group consisting of V, Nb, Ta and mixture thereof supported on a support comprising titania for a time sufficient to convert at least a portion of said $H_2S$ and CO to methanethiol, wherein said conversion reaction occurs with the $H_2S$ in the gaseous phase and wherein at least a portion of said supported oxide is in a non-crystalline form.

10. The process of claim 9 wherein said reaction pressure is below about 226 psig.

11. The process of claim 10 wherein said reaction temperature ranges between from about 225°–450° C.

12. The process of claim 11 wherein the ratio of $H_2S$ to CO in said gaseous feed ranges between about 1/4 to 40/1 on a mole basis.

13. The process of claim 12 wherein said reaction temperature ranges between about 250°–400° C.

14. The process of claim 13 wherein said ratio of $H_2S$ to CO in said gaseous feed ranges between about 1/2 to 4/1.

15. The process of claim 14 wherein said reaction temperature ranges between about 300° to 400° C.

16. The process of claim 15 wherein said supported metal oxide comprises an oxide of vanadium.

17. The process of either of claims 13 or 16 wherein at least about 25 wt.% of said supported metal oxide is in a non-crystalline form.

18. A process for producing methanethiol from a gaseous feed comprising a mixture of CO and $H_2S$, said process contacting said feed at a temperature of at least about 225° C. with a catalyst comprising an oxide of a metal selected from the group consisting of (a) V and (b) mixtures of V with Nb, Ta and mixture thereof supported on titania, for a time sufficient to convert at least a portion of said CO and $H_2S$ to methanethiol and wherein at least about 25 wt.% of said supported oxide is in a non-crystalline form.

19. The process of claim 18 wherein the ratio of $H_2S$ to CO in said gaseous feed ranges between about 1/4 to 40/1 on a mole basis.

20. The process of claim 19 wherein said reaction temperature ranges between about 225° to 450° C.

21. The process of claim 20 wherein said ratio of $H_2S$ to CO in said gaseous feed ranges between about 1/2 to 4/1.

22. The process of claim 21 wherein said reaction temperature ranges between about 300° to 400° C.

23. The process of claim 22 wherein said reaction occurs in the gaseous phase.

* * * * *